(12) United States Patent
Kinoshita et al.

(10) Patent No.: US 9,539,444 B2
(45) Date of Patent: *Jan. 10, 2017

(54) HAIR CONDITIONING COMPOSITION AND LOW ENERGY METHOD OF PRODUCING THE SAME

(75) Inventors: Kouichi Kinoshita, Yokohama (JP); Reiji Miyahara, Yokohama (JP); Kenji Kurokawa, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 42 days.

This patent is subject to a terminal disclaimer.

(21) Appl. No.: 13/063,208

(22) PCT Filed: Feb. 3, 2010

(86) PCT No.: PCT/JP2010/051511
§ 371 (c)(1),
(2), (4) Date: Mar. 10, 2011

(87) PCT Pub. No.: WO2010/090219
PCT Pub. Date: Aug. 12, 2010

(65) Prior Publication Data
US 2011/0165110 A1    Jul. 7, 2011

(30) Foreign Application Priority Data
Feb. 3, 2009    (JP) .................. 2009-022911

(51) Int. Cl.
*A61Q 5/12* (2006.01)
*A61K 8/02* (2006.01)
*A61K 8/04* (2006.01)
*A61K 8/34* (2006.01)
*A61K 8/36* (2006.01)
*A61K 8/39* (2006.01)

(52) U.S. Cl.
CPC ............. *A61Q 5/12* (2013.01); *A61K 8/042* (2013.01); *A61K 8/342* (2013.01); *A61K 8/345* (2013.01); *A61K 8/361* (2013.01); *A61K 8/39* (2013.01)

(58) Field of Classification Search
None
See application file for complete search history.

(56) References Cited

U.S. PATENT DOCUMENTS

| | | | |
|---|---|---|---|
| 4,183,917 A * | 1/1980 | Iwao | A61K 8/06 424/70.11 |
| 4,421,740 A * | 12/1983 | Burton | A61K 8/342 424/70.13 |
| 2003/0008790 A1 | 1/2003 | Carew et al. | |
| 2005/0013837 A1* | 1/2005 | Belmar et al. | 424/401 |
| 2006/0188460 A1 | 8/2006 | Ambrosen et al. | |
| 2007/0041929 A1 | 2/2007 | Torgerson et al. | |
| 2009/0142381 A1 | 6/2009 | Agarelli et al. | |
| 2011/0135587 A1 | 6/2011 | Kinoshita et al. | |

FOREIGN PATENT DOCUMENTS

| | | |
|---|---|---|
| CN | 101198311 A | 6/2008 |
| CN | 101212950 | 7/2008 |
| EP | 2316414 | 5/2011 |
| GB | 2383950 | 7/2003 |
| JP | 9-165321 | 6/1997 |
| JP | 2003-300812 | 10/2003 |
| JP | 2004-534807 | 11/2004 |
| JP | 2005-516026 | 6/2005 |
| WO | 03/000205 | 1/2003 |
| WO | 2006/119042 | 11/2006 |
| WO | 2010/016591 | 2/2010 |

OTHER PUBLICATIONS

Machine translation of JP09-165321, original document published Jun. 1997.*
International Search Report for corresponding PCT/JP2010/051511, mailed May 18, 2010, two pages.
U.S. Appl. No. 13/057,329, filed Feb. 3, 2011, 41 pages.
Espacenet bibliographic data for JP 2003300812, one page.
Espacenet bibliographic data for JP 2005516026, one page.
Espacenet bibliographic data for JP 2004534807, one page.
Espacenet bibliographic data for JP 9165321, one page.
Japanese Patent Abstract for Publication No. 2003-300812 published Oct. 21, 2003, seven pages.
International Preliminary Report on Patentability mailed May 18, 2010, five pages.
Extended European Search Report dated Jul. 10, 2012, Shiseido Co. Ltd., Application No. 10738550, eight pages.

* cited by examiner

*Primary Examiner* — Nissa Westerberg
(74) *Attorney, Agent, or Firm* — Rankin, Hill & Clark LLP

(57) ABSTRACT

A hair conditioning composition containing very little water from which a hair conditioner can be easily produced by diluting with water, and a low energy production method thereof.

A hair conditioning composition including (a) 10 to 90% by mass of specifically structured higher alcohols and/or derivatives thereof, (b) 5 to 35% by mass of cationic surfactant, and (c) a polyhydric alcohol and/or polyethylene glycol having a melting point of 70° C. or less, wherein the melting point of a gel which is formed from (a) and (b) in the composition is 70° C. or less, the water content is 10% by mass or less, and the molar ratio of (a) to (b) is 2.5 or more to less than 6.0. Also, a low energy method of producing a hair conditioner by melting the hair conditioning composition under heating at the temperature of the melting point of gel or more to 70° C. or less, and diluting it with water in an amount of 3 to 15 times by mass.

8 Claims, No Drawings

HAIR CONDITIONING COMPOSITION AND LOW ENERGY METHOD OF PRODUCING THE SAME

RELATED APPLICATIONS

This application claims the priority of Japanese Patent Application No. 2009-022911 filed on Feb. 3, 2009 which is incorporated herein by reference.

FIELD OF THE INVENTION

The present invention relates to a hair conditioning composition, and particularly relates to a hair conditioner that is diluted when used and a low energy method of producing the same.

BACKGROUND OF THE INVENTION

Many of conventional hair conditioners adopt a form in which components are dissolved or dispersed in a large amount of water. Products with such form are basically realized by stably dispersing various formulation components in water that is an excellent solvent. In addition, in most hair conditioners, a cationic surfactant that is a basic component forms a lamellar α-gel structure in combination with a higher alcohol and water or via emulsification of oil and water, and the hair conditioner may turn into a high-viscosity gel. Therefore, also for viscosity control of a composition, it has been preferred to contain a large amount of water up to an extent that would not impair its usability and its texture by excessively diluting the components.

On the other hand, the product containing a large amount of water requires energy for transportation and transfer for its weight and bulkiness. In addition, water or the composition containing water has a problem in energy efficiency on the product manufacturing since energy consumption is excessively required for its heating and cooling. Furthermore, the product containing a large amount of water is susceptible to the conditions during production and storage (history of load stress and temperature) and is difficult to maintain qualities such as viscoelasticity for a long period of time.

Therefore, reduction in the water content of hair conditioner leads to quality maintenance as well as reductions in a lot of energy consumption, production and transportation, and in product cost, and is believed to be one of the breakthroughs in the art also from the viewpoint of improvement in global environment.

Patent Literature 1: PCT Japanese Translation Patent Publication No. 2004-534807
Patent Literature 2: PCT Japanese Translation Patent Publication No. 2005-516026
Patent Literature 3: Japanese Unexamined Patent Publication No. 2003-300812

DISCLOSURE OF THE INVENTION

Problem to be Solved by the Invention

First, as means for reducing the water content of a hair conditioning composition, application of freeze drying or spray drying widely used for foods and the like can be considered. However, in order to carry out the means, it is first required to produce a normal hair conditioner, and the energy to put the normal hair conditioner to a drying process is further added. Therefore, the energy efficiency in the production process is worse than that of a conventional hair conditioner. Also, the drying process has caused a problem such that scent of the product is impaired, or equipment investment is required for mass production. Therefore, the production of a concentrated hair conditioner in which the water content is reduced from the first has been desired.

As a hair conditioning composition with a low water content, for example, a solid hair conditioning agent is disclosed (Patent Literature 1). This is solidified (stick) form obtained by reducing the water content of a conventional hair conditioning agent and can be used by rubbing into hair.

This hair conditioning agent is the one where water of the conventional formulation components is reduced, in other words, water is used as a concentrated medium. In this case, the amount of water contained is reduced, and viscosity is markedly increased during production, and thus, stirring and mixing of the components are markedly prevented with a reduction of the water content. Therefore, there is a limit to the amount of water that can be removed from the hair conditioning agent using water as a medium.

In addition, as another invention of a solid hair conditioning agent with a low water content, an agent in which relatively stable production is made possible by dissolving the components into oil such as warmed cocoa butter has been developed (Patent Literature 2). However, with a use mode of rubbing into hair, it is difficult to homogeneously apply the conditioner to entire use site, and also in the nature of directly rubbing solidified oil into hair, the solid hair conditioning agent falls short of a conventional water-based hair conditioning agent in an aspect of ease of handling such as stickiness or the like.

In other words, in spite of the problem of viscosity increase of the system, it is possible to reduce the water content of the hair conditioning composition to some extent and substitute water with oil, while it is difficult to concentrate conditioning components with containing almost no water. Therefore, a concentrated hair conditioner that is a type to be diluted with water before use is not yet realized as a product.

Patent Literature 3 describes a flake form cosmetic base composition containing a high concentration of a cationic surfactant with a specific structure that can be used as a conditioning component. However, while the base composition has very high hygroscopicity, the base composition has low water absorbability and is difficult to be diluted with water. Therefore, the base composition cannot be used as a concentrated hair conditioner as it is.

The present invention has been made in view of the problems, and an object of the present invention is to provide an easily-handled hair conditioning composition with a very low water content and a low energy method of producing the same.

Means to Solve the Problem

The present inventors have extensively investigated and consequently found that, in compositions containing a polyhydric alcohol and/or polyethylene glycol as a medium of a higher alcohol and a cationic surfactant that are conditioning components, those having a melting temperature of a gel by these components of 70° C. or less can be an easily-handled hair conditioning composition that can be produced at low energy, thereby accomplishing the present invention.

More specifically, the hair conditioning composition of the present invention is a composition comprising:
(a) 10 to 90% by mass of one or more components selected from higher alcohols having 16 carbon atoms or more, higher fatty acids having 16 carbon atoms or more, and/or derivatives thereof represented by the following formulas (I) and (II):

$$R^1-O-(-(CH_2)_y-O-)_x-H \quad (I)$$

wherein $R^1$ is a straight chain or branched fatty acid residue having 10 to 24 carbon atoms, and each of x and y is an integer of 1 to 3,

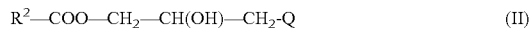
$$R^2-COO-CH_2-CH(OH)-CH_2-Q \quad (II)$$

wherein $R^2$ is a straight chain or branched fatty acid residue having 9 to 23 carbon atoms, and Q is H or OH;
(b) 5 to 35% by mass of a cationic surfactant; and
(c) a polyhydric alcohol and/or polyethylene glycol having a melting point of 70° C. or less, characterized in that the endothermic peak of a gel which is formed from (a) and (b) in the composition is 70° C. or less as measured by a differential scanning calorimeter (DSC) and that the water content is 10% by mass or less and the molar ratio of (a) to (b) is 2.5 or more to less than 6.0.

Furthermore, the present inventors have found that specific polyhydric alcohol and/or polyethylene glycol is applied as a medium, and a component selected from higher alcohols, higher fatty acids, and/or derivatives thereof, and a cationic surfactant are contained in a specific molar ratio, thereby providing high water absorbability to the hair conditioning composition.

More specifically, in the hair conditioning composition, (c) is preferably one or more selected from propylene glycol, dipropylene glycol, 1,3-butylene glycol, isopentyldiol, glycerin, and/or polyethylene glycol with a molecular weight of 5,000 or less.

Furthermore, the hair conditioning composition of the present invention is preferably a solid or paste form at ambient temperature.

In addition, the hair conditioning composition is preferably a hair conditioning precursor composition.

Also, the hair conditioning composition is preferably diluted with water at a dilution rate of 3 to 15 times by mass before use.

Furthermore, the low energy method of producing the hair conditioning composition of the present invention is characterized by melting the hair conditioning composition as a precursor composition under heating at the temperature of the melting point of a gel or more to 70° C. or less, and diluting it with water in an amount of 3 to 15 times by mass.

Moreover, the method of using the hair conditioner of the present invention is characterized by diluting the hair conditioning composition as a precursor composition with water in an amount of 3 to 15 times by mass to prepare the hair conditioner, and using it.

Effect of the Invention

According to the present invention, a concentrated type hair conditioning composition that can be diluted with water before its application to hair can be obtained. The composition makes it possible to reduce energy consumption during production and transportation and reduce energy consumption required for use and disposal of a container and an outer package without degrading the quality as a hair conditioner. In addition, the hair conditioning composition of the present invention is compact as it contains very little water when used as it is, and is can be used in an easily-handled form, thereby having a great advantage in carrying on the plane and for outdoor use.

Moreover, according to the present invention, the energy involved in the conventional hair conditioner production can be reduced. When a hair conditioner is produced in a conventional production method, the steps are generally as follows: heating all of water (about 70 to 95% though it depends on the formulation), higher alcohols, cationic surfactants, and the moisturizers such as polyhydric alcohols to 70° C. or more, mixing them homogenously, and cooling the mixture to 35° C. or less by letting it though a cooling equipment such as a scraped surface heat exchanger. However, in the present invention, all of the energy involved in warming water, providing the electric power to a cooling equipment such as a scraped surface heat exchanger, and washing the cooling equipment can be reduced by warming, to the temperature of the melting point of a gel or more to 70° C. or less, the hair conditioning composition containing only 10% by mass or less of water and dissolving it in water. Thus, the present invention can contribute to reducing the emissions of carbon dioxide.

BEST MODE FOR CARRYING OUT THE INVENTION

When a hair conditioning composition of the type which is diluted with water before use is produced, a mode in which the water of a conventional hair conditioner containing a large amount of water is reduced, and this water is compensated when used can be first considered. However, when a general hair conditioner is produced with low water content, in a rinse gel (α gel) with a higher alcohol and/or a higher fatty acid that is a general formulation component and a cationic surfactant using water as a medium, an interlayer spacing of the lamellar structure narrows. Therefore, the gel has very high viscosity by two-fold concentration or so, and it is difficult to stir and mix the components upon production of a hair conditioning composition. With the two-fold concentration or so and the small amount of the production amount, it is not impossible to stir and mix against viscosity resistance caused by such low water. However, if a further highly concentrated hair conditioning composition is produced on a large scale, it is bound to require at least a huge amount of energy for stirring and mixing, and it is very difficult to stably produce a composition in which components are homogeneously mixed.

On the other hand, the hair conditioning composition of the present invention is a composition containing a polyhydric alcohol and/or polyethylene glycol having a melting point of 70° C. or less as a medium in place of the water, wherein the endothermic peak of a gel which is formed from the higher alcohol and/or higher fatty acid and a cationic surfactant in the composition is 70° C. or less as measured by a differential scanning calorimeter (DSC). According to the present invention, heated and melted polyhydric alcohol and/or polyethylene glycol is stirred and mixed with previously heated and melted other components under heating, thereafter the mixture is cooled, whereby homogeneous mixture can be obtained without generating a marked viscosity resistance as in the case of using water as a medium.

In addition, the hair conditioning composition uses specific polyhydric alcohol and/or a polyethylene glycol having a molecular weight within a specific range, thereby immediately absorbing water once water is added and turning into a conventional gel-type hair conditioner. In other words, the hair conditioning composition of the present invention encompasses an embodiment with an excellent texture both during production and during use.

Hereinbelow, the present invention will be described in detail.

First, the essential components of the present invention: (a) one or more components selected from higher alcohols, higher fatty acids, and derivatives thereof, (b) a cationic surfactant, and (c) a polyhydric alcohol and/or polyethylene glycol, will be described.

(a) One or More Components Selected from Higher Alcohols, Higher Fatty Acids, and Derivatives Thereof The hair conditioning composition of the present invention contains one or more components selected from higher alcohols, higher fatty acids, and derivatives thereof.

As the higher alcohols contained in the present invention, those normally used in cosmetics, pharmaceuticals, and the like can be used. Examples of the higher alcohols include straight chain alcohols (for example, lauryl alcohol, cetyl alcohol, stearyl alcohol, behenyl alcohol, myristyl alcohol, oleyl alcohol, cetostearyl alcohol, hardened rapeseed oil alcohol, and the like); and branched-chain alcohols (for example, monostearyl glyceryl ether (batyl alcohol), 2-decyltetradecynol, lanolin alcohol, cholesterol, phytosterol, hexyldodecanol, isostearyl alcohol, octyldodecanol, and the like).

In the present invention, the straight chain alcohols having 16 carbon atoms or more are preferably used, and the straight chain alcohols having 16 to 22 carbon atoms such as stearyl alcohol, behenyl alcohol, oleyl alcohol, and cetostearyl alcohol can be particularly preferably used.

In addition, the derivatives of higher alcohols contained in the present invention are a compound represented by the following formula (I).

$$R^1-O-(-(CH_2)_y-O-)_x-H \quad (I)$$

In the formula (I), $R^1$ is a straight chain or branched fatty acid residue having 10 to 24 carbon atoms, and each of x and y is an integer of 1 to 3. Examples of such compounds include polyoxyethylene (1) stearyl alcohol, polyoxyethylene (2) cetostearyl alcohol, polyoxypropylene (3) lauryl alcohol, and polyoxybutylene (2) cetyl alcohol.

In addition, as the higher fatty acids contained in the present invention, those normally used in cosmetics, pharmaceuticals, and the like can be also used. Examples of the higher fatty acid include lauric acid, myristic acid, palmitic acid, stearic acid, behenic acid, oleic acid, undecylenic acid, tall acid, isostearic acid, linolic acid, linoleic acid, eicosapentaenoic acid (EPA), docosahexaenoic acid (DHA), and palm oil fatty acid. These can be used alone or as a combination of two or more kinds. Particularly, in the present invention, the straight chain fatty acids having 16 carbon atoms or more are preferable, and the straight chain fatty acids having 16 to 22 carbon atoms such as palmitic acid, stearic acid, and behenic acid can be particularly preferably used among them.

In addition, the derivatives of higher fatty acids contained in the present invention are a compound represented by the following formula (II).

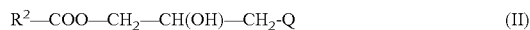

$$R^2-COO-CH_2-CH(OH)-CH_2-Q \quad (II)$$

In the formula (II), $R^2$ is a straight chain or branched fatty acid residue having 9 to 23 carbon atoms, and Q is H or OH. Examples of such compounds include monoglyceride stearate, propylene glycol monostearate, and monoglyceride oleate.

The hair conditioning composition of the present invention can contain the higher alcohols, the higher fatty acids, and/or derivatives thereof alone or as a combination of two or more kinds. Particularly, in the present invention, it is preferred that a higher alcohol and/or a higher alcohol derivative having a straight chain fatty acid residue having 16 to 22 carbon atoms is contained as the component (a).

(a) One or more components selected from higher alcohols, higher fatty acids, and derivatives thereof, in the hair conditioning composition of the present invention, can be contained in the range of 10 to 90% by mass and more preferably 20 to 50% by mass based on the composition, while it also depends on the amount of (b) cationic surfactant contained. When the amount of the component (a) contained is less than 10% by mass, energy reduction during production and transfer is not enough, and also viscoelasticity in the composition after dilution may be impaired.

(b) Cationic Surfactant

The hair conditioning composition of the present invention contains a cationic surfactant.

As the cationic surfactant contained in the present invention, those normally used in cosmetics, pharmaceuticals, and the like can be used. Particularly, a mono long-chain alkyl type quaternary ammonium salt represented by the following formula (III) is preferably used.

In the formula (III), $R^3$ represents a straight chain or branched alkyl group having 8 to 36 carbon atoms that may be substituted with a hydroxyl group, or $R^7-(Z1)_q-(Y1)_p-(W1)_m-$.

$R^7$ represents a straight chain or branched alkyl group having 8 to 36 carbon atoms that may be substituted with a hydroxyl group, Y1 represents a linkage group selected from $-CH_2CH_2-$, $-CH_2CH_2CH_2-$, and $-CH_2CH(OH)CH_2-$, W1 represents a linkage group selected from $-O-CH_2CH_2-$, and Z1 represents a linkage group selected from an amide bond ($-CONH-$), ether bond ($-O-$), and ester bond ($-COO-$). Each of p, q, and m represents an integer of 0 or 1.

In addition, $R^4$, $R^5$ and $R^6$ in the formula (III) represent an alkyl group having 1 to 3 carbon atoms or benzyl group that may be substituted with a hydroxyl group and may be the same or different. X represents a halogen atom, an alkyl sulfate group having 1 or 2 carbon atoms, or anion that may form a salt with quaternary ammonium such as a residue in which a hydrogen atom of an organic acid is removed.

Examples of the mono long-chain alkyl type quaternary ammonium salts represented by the formula (III) are lauryl trimethyl ammonium chloride, lauryl trimethyl ammonium bromide, myristyl trimethyl ammonium chloride, myristyl trimethyl ammonium bromide, cetyl trimethyl ammonium chloride, cetyl trimethyl ammonium bromide, stearyl trimethyl ammonium chloride, stearyl trimethyl ammonium bromide, behenyl trimethyl ammonium chloride, behenyl trimethyl ammonium bromide, cetyltrimethylammonium methanesulfonate, stearyltrimethylammonium methosulfate, myristyldimethylbenzylammonium chloride, cetyldimethylbenzylammonium chloride, stearyldimethylbenzylammonium chloride, octyldihydroxyethylmethylammonium chloride, 2-decyltetradecyltrimethylammonium chloride, 2-dodecylhexadecyltrimethylammonium chloride, stearoxypropyltrimethylammonium chloride, and N-(2-hydroxy-3-stearoxypropyl)-N,N-dimethylamine bromide.

Also, in the present invention, as a component to form the mono long-chain alkyl type quaternary ammonium salts of the formula (III), the mono long-chain alkyl type amine represented by the following formula (IV) and an organic acid can be contained in combination.

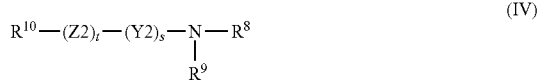

(IV)

In the formula (IV), $R^8$ and $R^9$ represent an alkyl group having 1 to 3 carbon atoms or benzyl group that may be substituted with a hydroxyl group and may be the same or different. $R^{10}$ represents a straight chain or branched alkyl group having 8 to 36 carbon atoms that may be substituted with a hydroxyl group.

In addition, Y2 represents a linkage group selected from $—CH_2CH_2—$, $—CH_2CH_2CH_2—$, and $—CH_2CH(OH)CH_2—$, W2 represents a linkage group selected from $—O—CH_2CH_2—$, and Z2 represents a linkage group selected from an amide bond ($—CONH—$), ether bond ($—O—$), and ester bond ($—COO—$). Each of s, t, and u represents an integer of 0 or 1.

The mono long-chain alkyl type amine represented by the formula (IV) and the organic acid suitable for the formulation into the present invention can be combined arbitrarily. Examples thereof include dimethylamide propylamide stearate-glutamic acid, diethylamide propylamide stearate-lactic acid, stearoxypropyl dimethylamide-malic acid, stearyl PG dimethylamine-glutamic acid, behenamidopropyl dimethylamine-succinic acid, and stearamidopropyl dimethanolamine-tartaric acid.

The hair conditioning composition of the present invention can contain the cationic surfactant alone or as a combination of two or more kinds.

The amount of (b) cationic surfactant contained in the composition of the present invention is preferably from 5 to 35% by mass and more preferably from 10 to 25% by mass based on the composition. When the amount of the component (b) contained is less than 5% by mass, texture and viscoelasticity in the composition after dilution may be insufficient, and energy reduction during production and transfer is not also sufficient. When the amount of the component (b) contained exceeds 35% by mass, stickiness may be caused in the composition, and the composition may not be homogeneously diluted. Also, skin irritation may be caused by the high formulation of the surfactant.

(c) Polyhydric Alcohol and/or Polyethylene Glycol

The hair conditioning composition of the present invention contains a water-soluble polyhydric alcohol and/or polyethylene glycol as a medium for the components.

In the temperature-rise measurement using a differential scanning calorimeter (DSC6100, manufactured by SII Nanotechnologies, Inc.), the polyhydric alcohol and/or polyethylene glycol contained in the present invention has an endothermic peak showing a melting point of the single body of 70° C. or less. Also, the polyhydric alcohol and/or polyethylene glycol contained in the present invention is a medium that makes the endothermic peak showing the melting point of a gel which is formed from (a) and (b) in the composition 70° C. or less, when the composition of the present invention is subjected to the temperature-rise measurement.

By using a medium with such characteristics, it is possible to homogeneously stir and mix the formulation components under heating and melting, and a dilutable concentrated hair conditioning composition that is a solid or paste at ambient temperature less than 70° C. can be obtained.

Considering storage stability and ease of handling after dilution as a hair conditioning composition, the polyhydric alcohol and/or polyethylene glycol having high viscosity (preferably 50,000 Pa·s or more) or becoming a solid in the temperature range that the storage or use of the composition is supposed (less than 50° C.) is more preferable. Furthermore, in view of water absorbability of the composition after dilution, the polyhydric alcohol and/or polyethylene glycol is preferably soluble in water for 20% by mass or more.

Examples of the polyhydric alcohol used in the present invention include propylene glycol, dipropylene glycol, 1,3-butylene glycol, isopentyldiol, glycerin, and/or polyethylene glycol with a molecular weight of 5,000 or less.

The hair conditioning composition of the present invention can contain the polyhydric alcohol and polyethylene glycol alone or as a combination of two or more kinds. Particularly, in being capable of producing the hair conditioning composition as powder or solid, and in being capable of providing high water absorbability to the composition, propylene glycol, dipropylene glycol, 1,3-butylene glycol, isopentyldiol, glycerin, and/or polyethylene glycol with a molecular weight of 5,000 or less are preferably used, and propylene glycol, dipropylene glycol, 1,3-butylene glycol, and/or isopentyldiol are particularly preferably used.

In the hair conditioning composition of the present invention, (c) polyhydric alcohol and/or polyethylene glycol can be contained in the range of 10 to 90% by mass based on the composition. When the amount of the component (c) contained is less than 10% by mass, homogeneous mixing of the formulation components and water absorbability of the composition may be insufficient.

Next, the compounding ratio of the essential components will be described.

In the hair conditioning composition of the present invention, the molar ratio of (a) one or more components selected from higher alcohols, higher fatty acids, and derivatives thereof to (b) cationic surfactant ((a)/(b)) is preferably 2.5 or more to less than 6.0, and particularly preferably 2.5 or more to 5.0 or less.

When the molar ratio is less than 2.5, in other words, the ratio of the cationic surfactant is high, hygroscopicity of the hair conditioning composition increases, and stickiness may be caused during use. Furthermore, water absorbability of the composition is reduced, and the separation of the composition (gel) from water may be caused when diluted. Also, with the increase in the amount of the cationic surfactant contained, skin irritation may increase.

When the molar ratio is 6.0 or more, in other words, the ratio of the one or more components selected from higher alcohols, higher fatty acids, and derivatives thereof is too high, the one or more components selected from higher alcohols, higher fatty acids, and derivatives thereof are likely to deposit in the hair conditioning composition or the diluted product thereof, i.e., the hair conditioner.

The hair conditioning composition of the present invention can be easily produced by melting and mixing (a) one or more components selected from higher alcohols, higher fatty acids, and derivatives thereof and (b) cationic surfactant under heating, mixing the mixture with separately melted (c) polyhydric alcohol and/or polyethylene glycol under heating, and thereafter cooling the mixture to room temperature. The temperature where the polyhydric alcohol and/or polyethylene glycol is heated and mixed with other components is not less than the melting temperature of a gel with the components and is 70° C. or less that is the temperature not less than the melting point of the polyhydric alcohol and/or polyethylene glycol. In other words, in the temperature range, the components of (a) to (c) are all in the melted state that can be mixed and also do not cause heat degradation. Furthermore, the components (a) to (c) in the temperature range are mixed, and thereafter, this mixture was cooled to less than 50° C., whereby a solid or paste composition which is excellent in ease of handling can be obtained.

Hereinbelow, the production example of the hair conditioning composition of the present invention is described.

(Production Example of Hair Conditioning Composition)

A cationic surfactant and one or more components selected from higher alcohols, higher fatty acids, and derivatives thereof are melted and mixed under heating at 130° C. In addition, a polyhydric alcohol and/or polyethylene glycol is heated at 70° C. or the temperature which is not less than the melting point of the polyhydric alcohol and/or polyethylene glycol. The melted mixture of the cationic surfactant and the one or more components selected from higher alcohols, higher fatty acids, and derivatives thereof is added thereto and mixed until being homogeneous while stirring, and thereafter, the resulting mixture is entirely cooled to 20 to 40° C., to obtain a hair conditioning composition. In the case where the composition is solid, the composition may be pulverized with a pulverizer as necessary.

The production example is not to limit the production conditions of the hair conditioning composition of the present invention, and for example, an optional component other than the essential components (a) to (c) can be also added to produce the composition. However, it is preferred to conduct the melting and mixing of the essential components (a) and (b). In the case of the composition obtained by pulverizing and mixing the essential components (a) to (c) without melting and mixing under heating, and molding the mixture, the effects tend to be insufficient as compared to those obtained by melting and mixing the components.

The hair conditioning composition of the present invention can be any dosage form depending on the desired product form, such as solid compositions with any size and shape, and powder, granular, or paste compositions. Examples of the product forms of the hair conditioning composition of the present invention include various forms depending on use conditions and the like, such as a form in which the powdered hair conditioning composition is individually-packaged by the amount used, a form in which the powdered composition is filled in a bottle and the required amount is taken out when used, a form in which the solid (bar) composition is put in a container when used and diluted, and are not particularly limited as far as it does not impair the effects of the present invention. In addition, in the industrial production of the general hair conditioner, the process of mixing the hair conditioning composition of the present invention with water can be applied.

As described above, it is particularly preferred that the hair conditioning composition of the present invention is used as a hair conditioning precursor composition before being applied to hair as a hair conditioner. In other words, the hair conditioning composition of the present invention can be used in the same manner as the conventional hair conditioner by diluting the appropriate amount with water when used. While the specific dilution rate in the present invention can be properly adjusted by the amounts of the essential components contained and the compounding ratio thereof, it is normally preferred that the composition of the present invention is diluted with water in an amount of 3 to 15 times by mass. The higher the temperature of dilution water is, the higher the dilution rate is, and even water at room temperature (20 to 30° C.) can sufficiently dilute the composition. In addition, the lower (less than 200 ppm) the hardness of dilution water is, the higher the dilution rate is, and even water with high hardness can sufficiently dilute the composition depending on a dilution method.

Also, the hair conditioning composition of the present invention may be used after diluting the required amount for each use on hands or heads or may be previously diluted in a container with an appropriate size in a mass and used as the conventional hair conditioner.

Also, when a hair conditioner is produced from the hair conditioning composition of the present invention, even on factory scale, it can be obtained by melting the composition under heating at the temperature of the melting point of gel or more to 70° C. or less, and diluting it with 3 to 15 times in mass of water. By producing a hair conditioner from the hair conditioning composition of the present invention, the cost for the storage and the energy for the production can be reduced compared with the conventional methods.

The hair conditioning composition of the present invention can contain other components normally used in cosmetics, pharmaceuticals, and the like within a range which does not impair the effects of the present invention, in addition to the essential components.

For example, while the hair conditioning composition of the present invention can contain water, the amount contained is preferably 10% by mass or less, more preferably 7% by mass or less, and further preferably 5% by mass or less, based on the composition of the present invention. Furthermore, in the present invention, it is most preferable that water is not substantially contained. When the amount of water contained exceeds 10% by mass, during the production of the composition, lowering of stirring and mixing properties due to viscosity increase and scattering of the components due to boiling may be caused. In addition, the formulation of excess water is not preferred since not only the solution of the problem in the present invention is insufficient, but also stickiness may be caused upon packaging and opening of the composition, and the transfer to a container and the like may be prevented.

Examples of other components which can be contained within the range that the effects of the present invention is not impaired include oils, powders, amphoteric surfactants, nonionic surfactants, natural polymers, synthetic polymers, thickeners, UV absorbers, metal ion sequestering agents, pH adjusters, skin nutrients, vitamins, antioxidants, antioxidant aids, and perfumes.

Examples of oils include liquid oils, solid oils, waxes, hydrocarbon oils, synthetic ester oils, and silicone oils.

Examples of liquid oils include avocado oil, *camellia* oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, *perilla* oil, soybean oil, peanut oil, tea seed oil, kaya oil, rice bran oil, *paulownia* oil, Japanese tung oil, *jojoba* oil, germ oil, and triglycerin.

Examples of solid oils include cacao butter, coconut oil, horse fat, hardened coconut oil, palm oil, beef tallow, mutton tallow, hardened beef tallow, palm kernel oil, pork tallow, beef bone tallow, Japan wax kernel oil, hardened oil, neatsfoot oil, Japan wax, and hardened castor oil.

Examples of waxes include beeswax, candelilla wax, cotton wax, carnauba wax, bayberry wax, Chinese wax, spermacetim, montan wax, rice bran wax, lanolin, kapok wax, lanolin acetate, liquid lanolin, sugar cane wax, isopropyl lanolate, hexyl laurate, reduced lanolin, *jojoba* wax, hard lanolin, shellac wax, POE lanolin alcohol ether, POE lanoline alcohol acetate, POE cholesterol ether, lanolin fatty acid polyethylene glycol, POE hydrogenated lanolin alcohol ether, and cetyl palmitate.

Examples of hydrocarbon oils include liquid paraffin, ozokerite, squalane, pristane, paraffin, ceresin, squalene, petrolatum, and microcrystalline wax.

Examples of silicone oils include linear polysiloxanes (such as dimethylpolysiloxane, methylphenylpolysiloxane, diphenylpolysiloxane, and dimethiconol); cyclic polysiloxanes (such as octamethylcyclotetrasiloxane, decamethylcyclopentasiloxane, and dodecamethylcyclohexasiloxane); silicon resin forming three-dimensional network structure; silicone rubber; various kinds of modified polysiloxane (such as amino modified polysiloxane, polyether modified polysiloxane (straight chain type, side-chain pendant type), alkyl modified polysiloxane, glyceryl modified polysiloxane, long-chain alkyl modified polysiloxane, and fluorine modified polysiloxane); and acrylic silicones.

Examples of powders include inorganic powders such as talc, kaolin, mica, sericite, muscovite, phlogopite, synthetic mica, lepidolite, biotite, vermiculite, bentonite, hectorite, laponite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate (calcined gypsum), calcium phosphate, fluorine apatite, hydroxyapatite, ceramic powder, metallic soap (e.g., zinc myristate, calcium palimitate, and aluminum stearate), and boron nitride; organic powders such as polyamide resin powder (nylon powder), polyethylene powder, polymethylmethacrylate powder, polystyrene powder, styrene-acrylic acid copolymer resin powder, benzoguanamine resin powder, poly (tetrafluroethylene) powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and lower order titanium oxide; inorganic purple pigments such as mango violet and cobalt violet; inorganic green pigments such as chrome oxide, chrome hydroxide, and cobalt titanate; inorganic blue pigments such as ultramarine and Prussian blue; pearl pigments such as titanium oxide coated mica, titanium oxide coated bismuth oxychloride, titanium oxide coated talc, colored titanium oxide coated mica, bismuth oxychloride, and fish scale flakes; metal powder pigments such as aluminum powder and copper powder; organic pigments such as zirconium, barium, or aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural colors such as chlorophyll and β-carotene.

Examples of amphoteric surfactants include imidazoline type amphoteric surfactants such as sodium 2-undecyl-N,N, N-(hydroxyethylcarboxymethyl)-2-imidazoline and 2-cocoyl-2-imidazolinium hydroxide-1-carboxyethyloxy)-2-sodium salt; betaine type surfactants such as 2-heptadecyl-N-carboxymethyl-N-hydroxyethylimidazolinium betaine, lauryldimethyl aminoacetate betaine, alkyl betaine, amidobetaine, and sulfobetaine.

Examples of lipophilic nonionic surfactants include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerol or polyglycerol fatty acid esters (such as glycerol mono-cotton seed oil fatty acid ester, glycerol monoerucate, glycerol sesquioleate, glycerol monostearate, glycerol α,α'-oleate pyroglutamate, and glycerol monostearate malate); propylene glycol fatty acid esters (such as propylene glycol monostearate); hardened castor oil derivatives; and glycerol alkyl ethers.

Examples of hydrophilic nonionic surfactants include POE-sorbitan fatty acid esters (such as POE-sorbitan monooleate, POE-sorbitan monostearate, and POE-sorbitan tetraoleate); POE sorbitol fatty acid esters (such as POE-sorbitol monolaurate, POE-sorbitol monooleate, POE-sorbitol pentaoleate, and POE-sorbitol monostearate); POE-glycerol fatty acid esters (such as POE-monooleates, POE-glycerol monostearate, POE-glycerol monoisostearate, and POE-glycerol triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic type surfactants (such as Pluronic); POE/POP-alkyl ethers (such as POE/POP cetyl ether, POE/POP 2-decyltetradecyl ether, POE/POP monobutyl ether, POE/POP hydrogenated lanolin, and POE/POP glycerol ether); tetra POE/tetra POP-ethylenediamine condensates (such as Tetronic); POE-castor oil or hardened castor oil derivatives (such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate); POE-beeswax lanolin derivatives (such as POE-sorbitol beeswax); alkanolamides (such as coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkylethoxydimethylamine oxides; and trioleyl phosphate.

Examples of natural water-soluble polymers include plant-derived polymers (such as gum arabic, tragacanth gum, galactan, guar gum, carob gum, gum karaya, locust bean gum, tamarind gum, carrageenan, pectin, agar, quince seed (quince), algae colloid (brown algae extract), starch (rice, corn, potato, and wheat), and glycyrrhizinate); microorganism-derived polymers (such as xanthan gum, dextran, succinoglucan, and pullulan); and animal-derived polymers (such as collagen, casein, albumin, and gelatin.)

Examples of semi-synthetic water-soluble polymers include starch polymers (such as carboxymethyl starch and methylhydroxypropyl starch); cellulose polymers (such as methyl cellulose, ethyl cellulose, methylhydroxypropyl cellulose, hydroxyethyl cellulose, sodium cellulose sulfate, dialkyldimethylammonium sulfate cellulose, hydroxypropyl cellulose, carboxymethyl cellulose, sodium carboxymethyl cellulose, crystalline cellulose, cellulose powder, hydrophobically modified compounds of these polymers (e.g., partially stearoxy modified compounds), and cation modified compounds of these polymers); alginate polymers (such as sodium alginate and propylene glycol alginate); and sodium pectate.

Examples of synthetic water-soluble polymers include vinyl polymers (such as polyvinyl alcohol, polyvinyl methyl ether, polyvinylpyrrolidone, and carboxyvinyl polymer); polyoxyethylene polymers (such as polyoxyethylene/polyoxypropylene copolymers, for example, polyethylene glycol 20,000, 40,000 or 60,000); poly(dimethyldiallylammonium halide) type cationic polymers (such as Merquat100 manufactured by Merck & Co., Inc.); dimethyldiallylammonium halide/acrylamido copolymer type cationic polymers (such as Merquat550 manufactured by Merck & Co., Inc.); acrylic polymers (such as sodium polyacrylate, polyethyl acrylate, and polyacrylamide); polyethyleneimine; cationic polymers; and magnesium aluminum silicate (veegum).

Examples of UV absorbers include benzoic acid UV absorbers (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, and N,N-dimethyl PABA butyl ester); anthranilic acid UV absorbers (such as homomenthyl N-acetylanthranilate); salicylic acid UV absorbers (such as amyl salicylate, menthyl salicylate, homomenthyl salicylate, octyl salicylate, phenyl salicylate, benzyl salicylate, and p-isopropanolphenyl salicylate); cinnamic acid UV absorbers (such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethyl-hexanoyl-diparamethoxy cinnamate); benzophenone UV absorbers (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor and 3-benzylidene-d,l-camphor; 2-phenyl-5-methylbenzoxazol; 2,2'-hydroxy-5-methylphenylbenzotriazol; 2-(2'-hydroxy-5'-t-octylphenyl) benzotriazol; 2-(2'-hydroxy-5'-methylphenylbenzotriazol; dianisoylmethane; 4-methoxy-4'-t-butyldibenzoylmethane; 5-(3,3-dimethyl-2-norbornylidene)-3-pentane-2-one; and triazine UV absorbers (such as 2-{4[(2-hydroxy-3-dodecyloxypropyl)oxy]-2-hydroxyphenyl)}-4,6-bis(2,4-dimethylphenyl)-1,3,5-triazine, and 2-{4[(2-hydroxy-3-tridecyloxypropyl)oxy]-2-hydroxyphenyl)}-4,6-bis(2,4-dimethylphenyl)-1,3,5-triazine).

Examples of metal ion sequestering agents include 1-hydroxyethane-1,1-diphosphonic acid, 1-hydroxyethane-1,1-diphosphonic acid 4Na salt, disodium edetate, trisodium edetate, tetrasorium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of pH adjusters include buffers such as lactic acid/sodium lactate, citric acid/sodium citrate, and succinic acid/sodium succinate.

Examples of vitamins include vitamins A, B1, B2, B6, C, and E and the derivatives thereof; pantothenic acid and the derivatives thereof; and biotin.

Examples of antioxidants include tocopherols, dibutylhydroxytoluene, butylhydroxyanisole, and gallic acid esters.

Examples of antioxidant aids include phosphoric acid, citric acid, ascorbic acid, maleic acid, malonic acid, succinic acid, fumaric acid, cephalin, hexametaphosphates, phytic acid, and ethylenediaminetetraacetic acid.

Examples of other components which can be contained include antiseptic (such as ethylparaben, butylparaben, 1,2-alkane diol, phenoxyethanol, and methylchloroisothiazolinone); antiphlogistic (such as glycyrrhizic acid derivatives, glycyrrhetinic acid derivatives, salicylic acid derivatives, hinokitiol, zinc oxide, and allantoin); whitening agent (such as saxifrage *sarmentosa* extract and arbutin); various extracts (such as *phellodendron* bark, goldthread, *lithospermum* root, *paeonia albiflora*, *swertia japonica*, birch, sage, loquat, carrot, *aloe, malva sylvestris* (mallow), iris, *vitis vinifera* (grape), *coix lacryma-jobi* (job's tears), *luffa cylindrica*, lily, saffron, *cnidium officinale*, ginger, *hypericum perforatum*, *ononis spinosa*, *allium sativum* (gerlic), *capsicum frutescens*, *citrus unshiu* peel, *angelica acutiloba*, and sea alga); activator agent (such as royal jelly, photosensitizers, and cholesterol derivatives); blood circulation accelerator (such as nonylic acid vanillylamide, nicotinic acid benzyl esters, nicotinic acid β-butoxy ethyl esters, capsaicin, Zingerone, Cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); antiseborrheic agent (such as sulfur and thianthol); anti-inflammatory agent (such as tranexamic acid, thiotaurine, and hypotaurine); and aromatic alcohols (such as benzyl alcohol and benzyloxy ethanol).

The hair conditioner in the present invention refers to overall cosmetics that provide conditioning effect to hair, and examples include hair rinse, hair treatment, and hair pack. The hair conditioner can include both type of being applied to hair and spread well overall when used and thereafter washed out (rinsed) with hot water, water or the like, and type of not being washed out after application.

Hereinbelow, the present invention is described in more detail with reference to Examples. However, the present invention is not limited to these Examples. The amount contained is all shown in % by mass unless otherwise described.

EXAMPLES

Selection of Water Soluble Solvent (Medium)

The mediums preferred in a hair conditioning composition were studied. The method for preparing the composition of each test example and the evaluation methods (DSC and water absorbability) are as follows.

Preparation of Hair Conditioning Composition

A mixture obtained by melting and stirring 13.9% by mass of stearyl trimethyl ammonium chloride and 32.6% by mass of stearyl alcohol (molar ratio of both: 3) under heating at 130° C. and 53.5% by mass of each medium shown in the following Table 1 previously melted were mixed under heating until homogeneous. Thereafter, the mixture was transferred to a container and cooled to room temperature to give a hair conditioning composition. These hair conditioning compositions are compositions in which general hair conditioners are concentrated into one-tenth and can be diluted with water or the like as a hair conditioning precursor composition and used.

Method for Evaluating Hair Conditioning Composition (Determination of DSC Endothermic Peak Temperature)

10 mg of each hair conditioning composition and 10 mg of dimethicone (20 cs) as a reference substance were each enclosed in an Ag closed cell and set to a holder of a differential scanning calorimeter (DSC6100, manufactured by SII Nanotechnologies, Inc.). The sample was heated from 30 to 200° C. at a heating rate of 2.0° C./min, and a temperature where heat absorption generated when the phase state of the composition changes was the maximum was recorded as a DSC endothermic peak temperature.

When a plurality of peak temperatures were obtained from the composition, based on the endothermic peak temperature of the contained component alone and the results of X-ray diffraction of the composition at each temperature, the peak temperatures were divided into DSC endothermic peak temperature derived from a medium, DSC endothermic peak temperature derived from a gel which was formed from a cationic surfactant and a higher alcohol, and DSC endothermic peak temperature of a higher alcohol which caused phase separation without contributing to the gel formation.

Among them, the endothermic peak temperatures derived from each medium and gel and the evaluations of the compositions by the following evaluation criteria are shown in Table 1.

(Evaluation Criteria of DSC Endothermic Peak Temperature of Composition)

O: The endothermic peak temperature showing the melting point of a gel in the composition is 70° C. or less, and the endothermic peak temperature showing the melting point of the medium is 70° C. or less.

X: The endothermic peak temperature showing the melting point of a gel in the composition exceeds 70° C., or the endothermic peak temperature showing the melting point of the medium exceed 70° C.

Method for Evaluating Water Absorbability

The appropriate amount of each hair conditioning composition was put in a mesh bag, and the bag was immersed into water. The dilution rates (Weight after Test/Weight Before Test) at 3 hours and 24 hours after the immersion were determined. The result of evaluating the dilution rates of each composition during each immersion time is shown in Table 1. The target values in Table 1 show the standard dilution rates in the actual use of the hair conditioning compositions prepared as above and are based on the amount of the cationic surfactant contained.

Production Test of Hair Conditioner 1 part of each hair conditioning composition was heated to 70° C. and mixed with 9 parts of ion-exchanged water. The mixture was stirred with a homogenizer for 1 minute, and the state was observed.

(Evaluation Criteria for Simplified Production of Composition)

O: A homogenous conditioner could be produced in one minute.

X: The mixture did not become homogenous in one minute.

molecular weight of 5,000 or less changed from a gel state to a liquid state with high viscosity at 70° C., and the hair conditioner could be easily produced by diluting the composition with water.

On the other hand, any of composition using, as a medium, erythritol, maltitol, sorbitol, D-mannit, xylitol, or polyethylene glycol with a molecular weight of 6,000 showed endothermic peak temperatures showing a gel melting at 70° C. or more. Thus, it was necessary to heat the composition to 70° C. or more for producing a hair conditioner.

In view of the above, in the determination of the DSC endothermic peak temperature, it became obvious that the hair conditioning composition having excellent stirring and mixing properties in a short time period and being suitable for the simplified production of hair conditioners can be obtained by allowing the melting point of a gel which is formed from the cationic surfactant and the higher alcohol to be 70° C. or less, and using, as a medium, polyhydric alcohol or polyethylene glycol having a melting point of 70° C. or less in the hair conditioning composition.

Thus, in the hair conditioning composition of the present invention, in terms of being simple in hair conditioner production, propylene glycol, isopentyldiol, dipropylene glycol, 1,3-butylene glycol, glycerin, and polyethylene glycol with a molecular weight of 5,000 or less are particularly preferably used as a medium.

<Molar Ratio of Higher Alcohol to Cationic Surfactant>

The hair conditioning compositions with the formulation compositions shown in Table 2 were evaluated according to the following evaluation methods. The evaluation results are shown in Table 2. These compositions are concentrated hair conditioners and can be diluted with water or the like as a hair conditioning precursor composition and used.

Method for Evaluating Hair Conditioning Composition (Determination of DSC Endothermic Peak Temperature of 10 Times Diluted Product)

For the hair conditioners obtained by diluting each hair conditioning composition with 9 times amount of water (10 times diluted product of original compositions), the endothermic peak temperature at 30 to 90° C. using the same apparatuses and methods as above was determined. Whether an endothermic peak other than a rinse gel at 30 to 90° C.

TABLE 1

| | Medium | Dipropylene glycol | 1,3-Butylene glycol | Isopentyldiol | Propylene glycol | Glycerin | PEG 400 | PEG 5000 | PEG 6000 | Sorbitol | Xylitol | Erythritol | Maltitol | D-mannite |
|---|---|---|---|---|---|---|---|---|---|---|---|---|---|---|
| DSC endothermic peak temperature [° C.] | Gel melting point | 43.5 | 47.4 | 43 | 45.4 | 63.8 | 66.6 | 69.9 | 72.4 | 73.2 | 73.2 | 72.3 | 74.6 | 75.2 |
| | Medium melting point | — | — | — | — | — | — | 55 | 59.6 | 67.9 | 88.1 | 116.1 | 136.5 | 162.3 |
| | Evaluation | O | O | O | O | O | O | O | X | X | X | X | X | X |
| Water absorbability | 3 hours later | 7.5 | 5 | 4.8 | 6.5 | 4.5 | 9 | 9.1 | 8.6 | 10 | 8.1 | 8.4 | 8.1 | 7.2 |
| | 24 hours later | 14.3 | 12 | 11.7 | 13 | 7.5 | 12 | 11.3 | 12.2 | 14 | 13.7 | 13.6 | 13.6 | 12.5 |
| | Target value | 7 | 7 | 7 | 7 | 7 | 7 | 7 | 7 | 7 | 7 | 7 | 7 | 7 |
| Simplified production of composition | Evaluation | O | O | O | O | O | O | O | X | X | X | X | X | X |

According to the evaluation of the DSC endothermic peak temperatures in Table 1, each composition using, as a medium, a dihydric alcohol with a low melting point such as propylene glycol, isopentyldiol, dipropylene glycol, or 1,3-butylene glycol, or glycerin or polyethylene glycol with a was generated was confirmed according to the determination, and the evaluation was carried out according to the following criteria. For the sample causing water discharge upon being diluted by 10 times, only a gel phase part was collected to carry out the determinations and evaluations.

(DSC Evaluation Criteria of 10 Times Diluted Product)
O: An endothermic peak was not found other than the endothermic peak of a rinse gel.
X: An endothermic peak was found other than the endothermic peak of a rinse gel.
Method for Evaluating Hair Conditioning Properties For the hair conditioners obtained by diluting each hair conditioning composition with 9 times amount of water (10 times diluted product of original compositions), an actual use test by 10 expert panels was conducted. In other words, each hair conditioner was applied to hair and washed with water, and thereafter conditioning properties of wet hair was evaluated with the following criteria. For the sample causing water discharge upon being diluted by 10 times, the evaluation was defined as X.
(Evaluation Criteria of Conditioning Properties)
O: 8 or more panels evaluated that hair was smooth after use.
Δ: 4 to 7 panels evaluated that hair was smooth after use.
X: 3 or less panels evaluated that hair was smooth after use.

TABLE 2

|  | Test Ex. 1 | Test Ex. 2 | Test Ex. 3 | Test Ex. 4 | Test Ex. 5 | Test Ex. 6 | Test Ex. 7 | Test Ex. 8 | Test Ex. 9 | Test Ex. 10 |
|---|---|---|---|---|---|---|---|---|---|---|
| Stearyl trimethyl ammonium chloride | 36 | 28.1 | 19.5 | 17 | 15 | 13.4 | 12.2 | 10.2 | 8.8 | 7.8 |
| Stearyl alcohol | 14 | 21.9 | 30.5 | 33 | 35 | 36.6 | 37.8 | 38.8 | 41.2 | 42.2 |
| Dipropylene glycol | 50 | 50 | 50 | 50 | 50 | 50 | 50 | 50 | 50 | 50 |
| Molar ratio of higher alcohol to cationic surfactant | 0.5 | 1 | 2 | 2.5 | 3 | 3.5 | 4 | 5 | 6 | 7 |
| Gel melting point [° C.] | 43.7 | 50.5 | 45.5 | 44.5 | 43.9 | 43.5 | 43.2 | 42.8 | 42 | 41.5 |
| DSC of 10 times diluted product | X | O | O | O | O | O | O | O | X | X |
| Conditioning property | X | X | Δ | O | O | O | O | O | Δ | X |

As shown in Table 2, in the hair conditioning compositions, the gel showed an almost constant good endothermic peak temperature, regardless of the molar ratio of the higher alcohol (stearyl alcohol) to the cationic surfactant (stearyl trimethyl ammonium chloride). However, 10 times diluted product of each test sample caused an endothermic peak other than a rinse gel at a molar ratio of 0.5 or less and 6.0 or more, and such compositions were not homogeneous.

In addition, the conditioning properties of the 10 times diluted product were excellent in the test example with a molar ratio of the higher alcohol to the cationic surfactant of 2.5 or more to less than 6.0 in the composition and were likely to be poor in hair smoothness after use in the test example with a molar ratio of 2.0 or less and 6.0 or more.

Based on the above results, in the hair conditioning compositions of the present invention, it is preferred that the molar ratio of the higher alcohol to the cationic surfactant is 2.5 or more to less than 6.0.

<Use of Higher Fatty Acid>

The results of determination and evaluation of the samples using a higher fatty acid as the component (a) of the present invention (hair conditioning precursor compositions) are shown in the following Table 3. In Table 3, each determination and evaluation regarding an endothermic peak temperature and water absorbability were carried out according to the evaluation methods described above, and the evaluation regarding hygroscopicity was carried out as follows. In this context, the DSC endothermic peak temperature in Table 3 includes that of "Gel of surfactant/higher fatty acid/polyhydric alcohol" corresponding to the gel melting point in Table 1 and that of "Gel derived form higher fatty acid". The evaluation for the DSC endothermic peak temperature is as mentioned above. The result is shown in Table 3.

Method for Evaluating Hygroscopicity

Each hair conditioning composition was spread all over a weighing dish and was each allowed to stand still under conditions at a temperature of 45° C. and a relative humidity of 75, 85, or 90% for 6 hours. The result of evaluating the rate of weight change of each composition in each humidity condition as hygroscopicity is shown in Table 1.

Rate of Weight Change=(Weight after Test−Weight Before Test)/(Weight Before Test)×100(%)

TABLE 3

|  |  | Test Ex. 11 | Test Ex. 12 | Test Ex. 13 | Test Ex. 14 | Test Ex. 15 | Test Ex. 16 |
|---|---|---|---|---|---|---|---|
| Stearyl trimethyl ammonium chloride |  | 13.9 | 13.9 | 13.9 | 13.9 | 13.9 | 13.9 |
| Palmitic acid |  | 6.7 | 16.3 | 10.0 | 13.3 | 16.7 |  |
| Stearic acid |  | 15.6 | 16.3 | 23.4 | 31.2 | 39.0 |  |
| Glyceryl monostearate |  |  |  |  |  |  | 27.7 |
| Dipropylene glycol |  | 63.8 | 53.5 | 52.7 | 41.6 | 30.4 | 58.4 |
| Molar ratio of higher alcohol (compound) to cationic surfactant |  | 2.0 | 3.0 | 3.0 | 4.0 | 5.0 | 2.0 |
| DSC endothermic peak temperature [° C.] | Gel of surfactant/higher fatty acid/polyhydric alcohol | 36.8 | 40.2 | 41.4 | 42.9 | 47.2 | 46.5 |
|  | Gel derived form higher fatty acid | 61.9 | 62.9 | 64.4 | 63.9 | 67.1 | — |
|  | Evaluation | O | O | O | O | O | O |
| Hygroscopicity (Rate of increased weight after 6 hours) | 90% RH | 24.0 | 21.0 | 23.5 | 22.0 | 22.0 | 31.5 |
|  | 85% RH | 18.5 | 16.5 | 18.0 | 12.5 | 9.5 | 25.0 |
|  | 75% RH | 10.5 | 7.5 | 6.5 | 4.0 | 1.5 | 12.0 |
| Water absorbability (Dilution rate after a given time) | 3 hours later | 3.4 | 3.3 | 3.9 | 3.5 | 5.2 | 2.3 |
|  | 24 hours later | 4.7 | 5.0 | 5.6 | 5.0 | 6.5 | 3.8 |
|  | Target value | 5 | 5 | 5 | 5 | 5 | 5 |

As shown in Table 3, among Test Examples 11 to 16 in which a higher fatty acid was contained as the component (a) of the present invention, all of those other than Test Example 11 were hair conditioning compositions that had a preferable DSC endothermic peak temperature and also were excellent in hygroscopicity and water absorbability, as well as in the case of using a higher alcohol and/or derivative thereof.

However, Test Example 11, having a lower molar ratio (2.0) of the cationic surfactant to the higher fatty acid, was slightly low in the water absorbability, and the dilution rate did not reach the target value.

Also, Test Example 16, in which a higher fatty acid compound was used instead of the higher fatty acid, had an insufficient water absorbability.

In view of the above, it is obvious that, in the hair conditioning compositions of the present invention, a higher fatty acid can be preferably used as the component (a). Also, as a result of further study, it was found that the molar ratio of the higher fatty acid to the cationic surfactant is preferably 2.5 or more to less than 6.0.

<Cationic Surfactant>

The determination and evaluation of the samples (hair conditioning precursor compositions) shown in Table 4 were carried out, and the cationic surfactant preferable as the component (b) of the present invention was studied. In Table 4, each determination and evaluation regarding an endothermic peak temperature, hygroscopicity, and water absorbability were carried out according to the methods described above. The results are shown in Table 4.

TABLE 4

|  |  | Test Ex. 17 | Test Ex. 18 |
|---|---|---|---|
| Stearyl trimethyl ammonium chloride | | 13.9 | |
| Stearamidopropyl dimethylamine | | | 11.8 |
| Palmitic acid | | 10.0 | 10.0 |
| Stearic acid | | 23.4 | 23.4 |
| Dipropylene glycol | | 52.7 | 54.8 |
| Molar ratio of higher alcohol (compound) to cationic surfactant | | 3.0 | 3.0 |
| DSC endothermic peak temperature [° C.] | Gel of surfactant/higher fatty acid/polyhydric alcohol | 41.4 | 39.9 |
| | Gel derived form higher fatty acid | 64.4 | — |
| | Evaluation | ○ | ○ |
| Hygroscopicity (Rate of increased weight after 6 hours) | 90% RH | 23.5 | 19.5 |
| | 85% RH | 18.0 | 17.0 |
| | 75% RH | 6.5 | 9.0 |
| Water absorbability (Dilution rate after a given time) | 3 hours later | 3.9 | 1.4 |
| | 24 hours later | 5.6 | 1.4 |
| | Target value | 5 | 5 |

As shown in Table 4, when a higher fatty acid was used as the component (a), a mono long-chain alkyl type quaternary ammonium salt (Test Example 19) as (b) cationic surfactant was used, whereby a hair conditioning composition excellent as a hair conditioning precursor composition could be obtained.

On the other hand, even when stearamidopropyl dimethylamine was contained together with the fatty acid, a composition having a sufficient water absorbability could not be obtained.

In view of the above, also in the hair conditioning compositions of the present invention using a higher fatty acid as the component (a), a mono long-chain alkyl type quaternary ammonium salt is preferably used as the component (b).

The formulation examples of the hair conditioning compositions of the present invention are shown below. However, the present invention is not limited to these formulation examples. The amount of the component contained is all shown in % by mass.

Formulation Example 1

Hair Treatment

Behenyl trimethyl ammonium chloride 13.0
Dicocoylethyl hydroxyethylmonium methosulfate 1.0
Cetyl alcohol 12.0
Stearyl alcohol 18.0
Stearic acid 0.3
Propylene glycol 26.2
Glycerin 5.0
Dimethicone (500 cs) 5.0
Dimethiconol (1000 cs) 5.0
Methylphenyl methicone 1.0
PEG-10 dimethicone 1.0
2-Octyldodecanol 0.5
Octyl palmitate 3.0
Mineral oil 2.0
*Jojoba* alcohol 0.5
Phenoxy ethanol 3.0
Perfume 3.5

(Production Method)

Behenyl trimethyl ammonium chloride, dicocoylethyl hydroxyethylmonium methosulfate, cetyl alcohol, stearyl alcohol, stearic acid, and propylene glycol were melted and stirred under heating at 80° C. and mixed until becoming homogeneous. Furthermore, other components were added thereto, stirred and mixed, and the mixture was transferred to a container and cooled to room temperature, to give a composition.

The resulting composition was not sticky, was excellent in ease of handling, and could be preferably used as a hair treatment by diluting with water by 6 times.

Formulation Example 2

Hair Conditioner

Stearyl trimethyl ammonium bromide 8.0
Stearamidopropyl trimethylammonium chloride 5.0
Distearyl dimethyl ammonium chloride 1.0
Stearyl alcohol 23.0
Behenyl alcohol 8.0
Isostearyl alcohol 0.5
Oleic acid monoglyceride 0.3
Isopentyldiol 30.1
Sorbitol 4.0
Dimethicone (100 cs) 5.0
(bis-isobutyl PEG-14/amodimethicone) copolymer 0.5
Isocetyl isostearate 2.0
2-Octyldodecanol 1.0
Octyl palmitate 3.0
Di(phytosteryl/octyldodecyl) lauroyl glutamate 1.0
*Camellia reticulata* Lindl. seed oil 1.0
Alpha-tocopherol 1.0
Phytosteryl macadamiate 1.0
POE(1)-1,2-dodecanediol 3.0
Vanillyl butyl ether 0.1
Menthol 1.0
Perfume 2.5

(Production Method)

The mixture obtained by melting and stirring stearyl trimethyl ammonium bromide, stearamidopropyl trimethylammonium chloride, distearyl dimethyl ammonium chloride, stearyl alcohol, behenyl alcohol, isostearyl alcohol, and oleic acid monoglyceride under heating at 140° C., and isopentyldiol and sorbitol previously melted were mixed under heating until homogeneous. Furthermore, other components were added thereto, stirred and mixed, and the mixture was transferred to a container and cooled to room temperature, to give a composition.

The resulting composition was not sticky, was excellent in ease of handling, and could be preferably used as a hair conditioner by diluting with water by 8 times.

Formulation Example 3

Hair Conditioner

Cetyl trimethyl ammonium chloride 5.0
Behenyl PG trimethyl ammonium chloride 5.0
Stearamidopropyl dimethylamine 2.0
Cetyl alcohol 20.0
Stearyl alcohol 20.0
Isostearic acid 0.5
1,3-Butylene glycol 24.0
Dipropylene glycol 5.0
Lactic acid 0.2
Amodimethicone (1000 cs) 5.0
Lauryl polyglyceryl-3 polydimethylsiloxyethyl dimethicone 0.5
PEG/PPG-30/10 dimethicone 0.5
PEG-10 dimethicone 1.0
Octyl lactate 2.0
Isononyl isononate 2.0
Squalane 0.2
Purified sesame oil 1.0
Orange oil 0.4
Rosemary oil 0.2
Methyl paraben 2.0
Propyl paraben 1.0
Perfume 2.5
(Production Method)

Cetyl trimethyl ammonium chloride, behenyl PG methyl ammonium chloride, stearamidopropyl dimethylamine, lactic acid, cetyl alcohol, stearyl alcohol, isostearic acid, 1,3-butylene glycol, and dipropylene glycol were melted and stirred under heating at 85° C. and mixed until becoming homogeneous. Furthermore, other components were added thereto, stirred and mixed, and the mixture was transferred to a container and cooled to room temperature, to give a composition.

The resulting composition was not sticky, was excellent in ease of handling, and could be preferably used as a hair conditioner by diluting with water by 10 times.

What is claimed is:

1. A hair conditioning composition comprising:
   (a) 20 to 50% by mass of one or more components selected from higher alcohols having 16 carbon atoms or more, higher fatty acids having 16 carbon atoms or more, and/or derivatives thereof represented by following formulas (I) and (II):

$$R^1-O-(-(CH_2)_y-O-)_x-H \quad (I)$$

wherein $R^1$ is a straight chain or branched fatty acid residue having 10 to 24 carbon atoms, and each of x and y is an integer of 1 to 3, $$R^2-COO-CH_2-CH(OH)-CH_2-Q \quad (II)$$

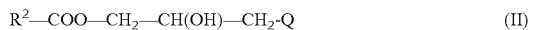

wherein $R^2$ is a straight chain or branched fatty acid residue having 9 to 23 carbon atoms, and Q is H or OH;
   (b) 5 to 35% by mass of a cationic surfactant; and
   (c) one or more selected from propylene glycol, dipropylene glycol, 1,3-butylene glycol, isopentyldiol, glycerin, and/or polyethylene glycol with a molecular weight of 5,000 or less,
   wherein (a) and (b) form an α gel in the composition,
   wherein endothermic peak of the α gel is 70° C. or less as measured by a differential scanning calorimeter (DSC),
   wherein water content is 10% by mass or less,
   wherein molar ratio of (a) to (b) is 2.5 or more to less than 6.0, and
   wherein the hair conditioning composition is a solid or paste form when a melted mixture of components (a), (b), and (c) is cooled to 20 to 40° C.

2. The hair conditioning composition according to claim 1, being a hair conditioning precursor composition.

3. A low energy method of producing a hair conditioning composition, comprising:
   the hair conditioning composition, as a precursor composition, according to claim 1 under heating at temperature of melting point of gel or more to 70° C. or less,
   diluting the hair conditioning composition according to claim 1 with water in an amount of 3 to 15 times by mass.

4. A method of using a hair conditioning composition, comprising:
   diluting the hair conditioning composition according to claim 1 with water in an amount of 3 to 15 times by mass to prepare a hair conditioner, and
   using the hair conditioner.

5. The hair conditioning composition according to claim 1, wherein the endothermic peak of the α gel is 43° C. or more and 70° C. or less.

6. A hair conditioner produced by diluting with water by 10 times a conditioning composition that comprises:
   (a) 20 to 50% by mass of one or more components selected from higher alcohols having 16 carbon atoms or more, higher fatty acids having 16 carbon atoms or more, and/or derivatives thereof represented by following formulas (I) and (II):

$$R^1-O-(-(CH_2)_y-O-)_x-H \quad (I)$$

wherein $R^1$ is a straight chain or branched fatty acid residue having 10 to 24 carbon atoms, and each of x and y is an integer of 1 to 3, $$R^2-COO-CH_2-CH(OH)-CH_2-Q \quad (II)$$

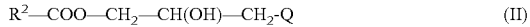

wherein $R^2$ is a straight chain or branched fatty acid residue having 9 to 23 carbon atoms, and Q is H or OH;
   (b) 5 to 35% by mass of a cationic surfactant; and
   (c) one or more selected from propylene glycol, dipropylene glycol, 1,3-butylene glycol, isopentyldiol, glycerin, and/or polyethylene glycol with a molecular weight of 5,000 or less,
   wherein (a) and (b) form an α gel in the composition,
   wherein endothermic peak of the a gel is 70° C. or less as measured by a differential scanning calorimeter (DSC),
   wherein water content is 10% by mass or less, wherein molar ratio of (a) to (b) is 2.5 or more to less than 6.0, and wherein the hair conditioning composition is a solid or paste form when a melted mixture of the components (a), (b), and (c) is cooled to 20 to 40° C.; and the hair conditioner is in a gel state.

7. A hair conditioner produced by diluting with water by 10 times a conditioning composition that comprises:
   (a) 20 to 50% by mass of one or more components selected from higher alcohols having 16 carbon atoms or more, higher fatty acids having 16 carbon atoms or more, and/or derivatives thereof represented by following formulas (I) and (II):

wherein $R^1$ is a straight chain or branched fatty acid residue having 10 to 24 carbon atoms, and each of x and y is an integer of 1 to 3,

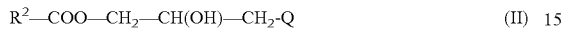

wherein $R^2$ is a straight chain or branched fatty acid residue having 9 to 23 carbon atoms, and Q is H or OH;
   (b) 5 to 35% by mass of a cationic surfactant; and
   (c) one or more selected from propylene glycol, dipropylene glycol, 1,3-butylene glycol, isopentyldiol, glycerin, and/or polyethylene glycol with a molecular weight of 5,000 or less,
   wherein (a) and (b) form an α gel in the composition, wherein endothermic peak of the a gel is 70° C. or less as measured by a differential scanning calorimeter (DSC),
   wherein water content is 10% by mass or less, wherein molar ratio of (a) to (b) is 2.5 or more to less than 6.0, and wherein the hair conditioning composition is a solid or paste form when a melted mixture of the components (a), (b), and (c) is cooled to 20 to 40° C.;
   and the hair conditioner is in an α gel state.

8. The hair conditioning composition according to claim 1, component (c) is disposed in an interlayer spacing of lamellar structures of the α gel formed by components (a) and (b).

* * * * *

UNITED STATES PATENT AND TRADEMARK OFFICE
CERTIFICATE OF CORRECTION

PATENT NO. : 9,539,444 B2
APPLICATION NO. : 13/063208
DATED : January 10, 2017
INVENTOR(S) : Kouichi Kinoshita et al.

It is certified that error appears in the above-identified patent and that said Letters Patent is hereby corrected as shown below:

In the Claims

Column 22, (Claim 3), delete Lines 21-23 "the hair conditioning composition, as a precursor composition, according to claim 1 under heating at temperature of melting point of gel or more to 70°C or less,"

Signed and Sealed this
Twenty-seventh Day of February, 2018

Andrei Iancu
*Director of the United States Patent and Trademark Office*